United States Patent [19]
Rebeiz et al.

[11] Patent Number: 5,300,526
[45] Date of Patent: * Apr. 5, 1994

[54] PORPHYRIC INSECTICIDES

[75] Inventors: Constantin A. Rebeiz, Urbana; John A. Juvik, Champaign; Carole C. Rebeiz, Urbana, all of Ill.

[73] Assignee: The Board of Trustees of the University of Illinois, Urbana, Ill.

[*] Notice: The portion of the term of this patent subsequent to Apr. 6, 2010 has been disclaimed.

[21] Appl. No.: 795,367

[22] Filed: Nov. 20, 1991

Related U.S. Application Data

[60] Division of Ser. No. 294,132, Jan. 9, 1989, Pat. No. 5,200,427, which is a continuation-in-part of Ser. No. 144,883, Jan. 13, 1988, abandoned, which is a continuation-in-part of Ser. No. 895,529, Aug. 11, 1986, Pat. No. 5,127,938, which is a continuation of Ser. No. 754,092, Jul. 15, 1985, abandoned, which is a continuation-in-part of Ser. No. 634,932, Jul. 27, 1984, abandoned.

[51] Int. Cl.⁵ .............................. A01N 37/44
[52] U.S. Cl. ................... 514/561; 514/292; 514/334; 514/557
[58] Field of Search ............... 514/292, 334, 561, 557

[56] References Cited

U.S. PATENT DOCUMENTS

| | | | |
|---|---|---|---|
| 3,043,675 | 7/1962 | Steinhards et al. | 71/94 |
| 3,274,206 | 9/1966 | Wilbert et al. | 71/94 |
| 3,804,845 | 4/1974 | Moore | 546/259 |
| 3,934,369 | 1/1976 | Rebeiz | 47/58 |
| 4,319,916 | 3/1982 | Abdulla | 71/94 |
| 4,322,241 | 3/1982 | Pissiotas et al. | 71/94 |
| 4,330,321 | 5/1982 | Johnson | 71/94 |
| 4,360,677 | 11/1982 | Doweyko et al. | 546/294 |
| 4,383,850 | 5/1983 | Handte et al. | 71/88 |
| 4,383,851 | 5/1983 | Rogers et al. | 71/94 |
| 5,127,938 | 7/1992 | Rebeiz | 71/113 |

FOREIGN PATENT DOCUMENTS

| | | |
|---|---|---|
| 56845/60 | 1/1963 | Australia . |
| 56849/60 | 1/1963 | Australia . |
| 509454 | 10/1930 | Fed. Rep. of Germany . |
| 8600785 | 2/1986 | World Int. Prop. O. . |

*Primary Examiner*—Allen J. Robinson
*Assistant Examiner*—B. Bembenick
*Attorney, Agent, or Firm*—Curtis, Morris & Safford

[57] ABSTRACT

Insecticidal compositions comprising one or more compounds selected from the group consisting of delta-aminolevulinic acid, inducers of delta aminolevulinic acid, and enhancers of delta-aminolevulinic acid conversion to photodynamic tetrapyrroles; and methods of making and using same.

19 Claims, 1 Drawing Sheet

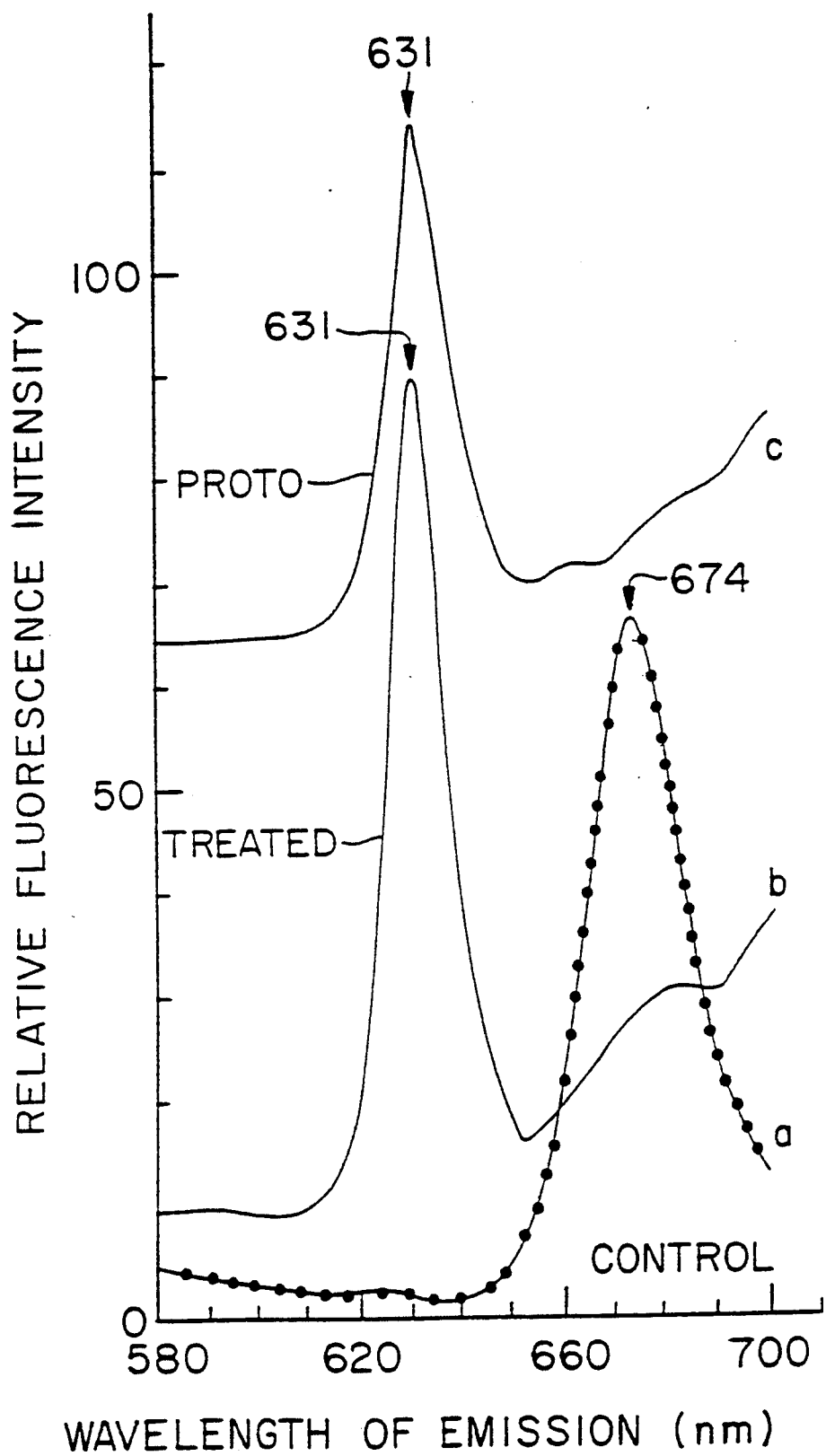
FIG. I

PORPHYRIC INSECTICIDES

This application is a division of copending application Ser. No. 07/294,132, filed Jan. 9, 1989, (U.S. Pat. No. 5,200,427), which in turn is a continuation-in-part of copending application Ser. No. 144,883, filed Jan. 13, 1988, now abandoned; which in turn is a continuation-in-part of copending application Ser. No. 895,529, filed Aug. 11, 1986 (U.S. Pat. No. 5,127,938); which is a continuation of application Ser. No. 754,092, filed Jul. 15, 1985, now abandoned; which in turn is a continuation-in-part of application Ser. No. 634,932, filed Jul. 27, 1984, now abandoned.

The invention described herein was made in the course of work supported by grants from the U.S. Department of Agriculture, the National Science Foundation, the University of Illinois, the Illinois Agricultural Experiment Station, and the John P. Trebellas Photobiotechnology Research Endowment.

This invention pertains to insecticidal compositions and methods, and more particularly to insecticidal compositions and methods for elevating endogenous tetrapyrrole levels in insects.

Copending application U.S. Ser. No. 895,529 (U.S. Pat. No. 5,127,938) describes herbicidal compositions comprising one or more compounds selected from the group consisting of delta-aminolevulinic acid, inducers of delta-aminolevulinic acid in plants, enhancers of delta-aminolevulinic acid conversion to photodynamic tetrapyrroles in plants, and inhibitors of conversion of divinyl tetrapyrroles to monovinyl tetrapyrroles in plants; methods for inducing the accumulation of photodynamic tetrapyrroles in living plants using said compositions, and methods of killing plants using said compositions. However, said compositions have not previously been known or described as insecticides.

The following terms, as used hereinabove and below, have the following meaning unless expressly stated to the contrary: ALA=delta-aminolevulinic acid; Chl=chlorophyll; Chlide=chlorophyllide; Coprogen=coproporphyrinogen; DP=dipyridyl; DV=divinyl; Mg-Proto=Mg-protoporphyrin IX; MV=monovinyl; PA=phenanthroline; PBG=porphobilinogen; PChl=protochlorophyll; PChlide=protochlorophyllide; Pheo=pheophytin; Pheobide=pheophorbide; Proto=protoporphyrin IX; Protogen=protoporphyrinogen; Uro=uroporphyrin octamethyl ester; and Urogen=uroporphyrinogen. The terms Proto, Mg-Proto, PChlide, Chlide, Chl, Pheo, and Pheobide refer to pools made up of MV and/or DV components unless explicitly preceeded by a MV or DV designation.

BRIEF DESCRIPTION OF THE DRAWINGS

FIG. 1: (a) hexane-extracted acetone extract of control larvae; the emission peak at 674 nm is that of MV Pheo a; (b) extract of treated larvae; (c) authentic DV Proto in hexane-extracted acetone.

Delta-aminolevulinic acid, a five-carbon amino acid, is found in most living animal and plant cells and is the primary tetrapyrrole precursor. It is available from a variety of specialty chemical sources, e.g. Sigma Chemical Co., St. Louis, Mo. In plants, ALA is a precursor of chlorophyll via a 6-branched pathway involving protoporphyrinogen, protoporphyrin, Mg-protoporphyrin, longer wavelength metalloporphyrins, protochlorophyll, and chlorophyllide [see FIG. 1 of copending application U.S. Ser. No. 895,529(U.S. Pat. No. 5,127,938)]. In insects, ALA is converted to protoheme (ferrous protoporphyrin IX) via a pathway involving porphobilinogen, uroporphyrinogen, coproporphyrinogen, protoporphyrinogen, protoporphyrin IX, and ferrous protoporphyrin IX (i.e. protoheme):

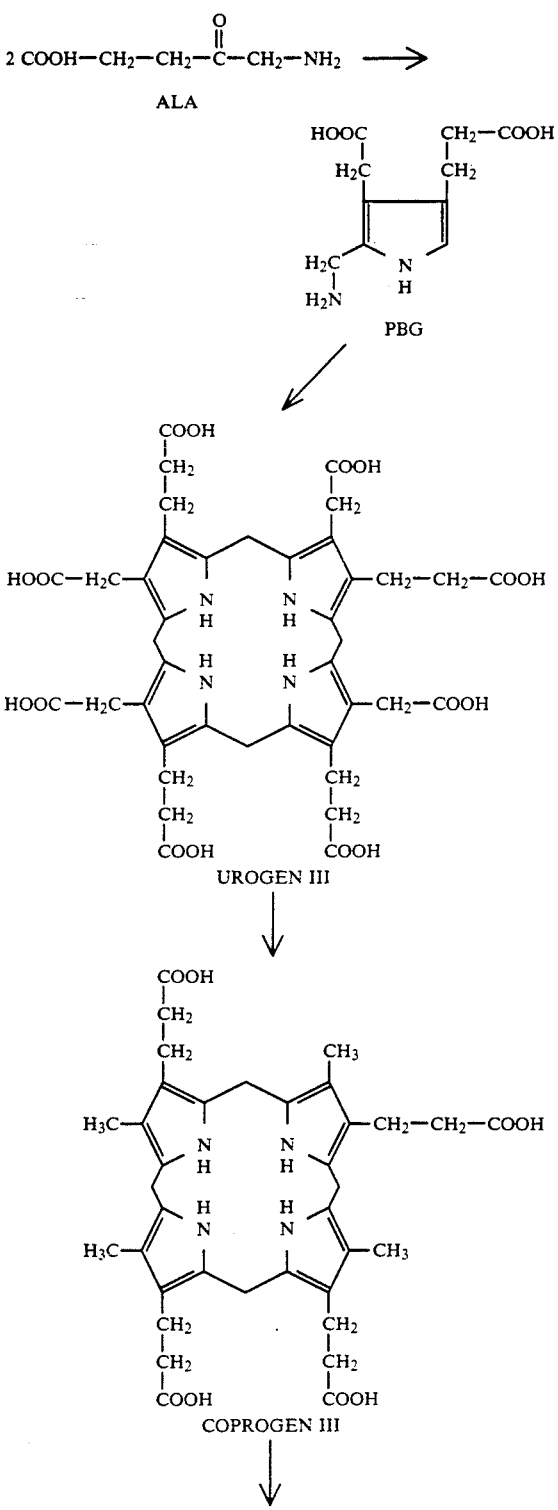

FLOWCHART A:

FLOWCHART A: -continued

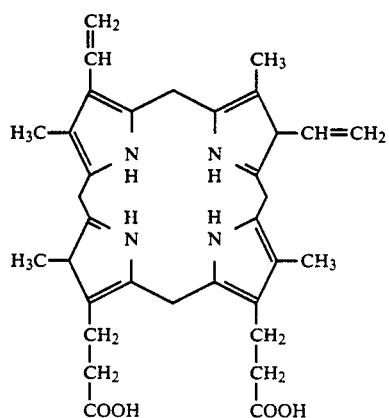

DV PROTOGEN IX

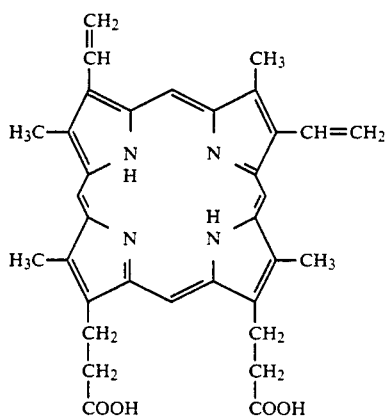

DV PROTO IX

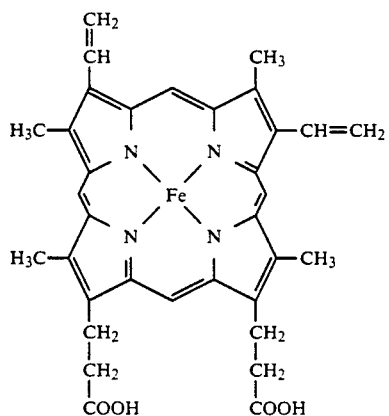

Fe-Proto (Protoheme)

FLOWCHART A: -continued

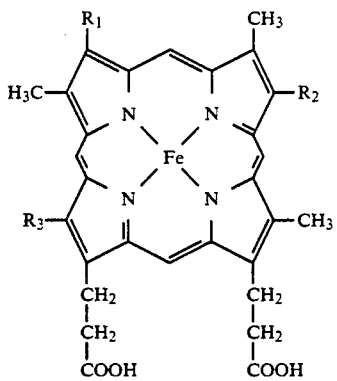

Heme A $R_1 =$

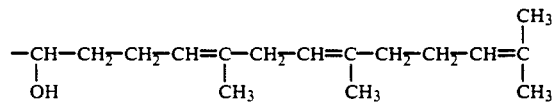

$R_2 = -CH=CH_2$ $R_3 = -CHO$

Heme C $R_1 = R_2 = $ 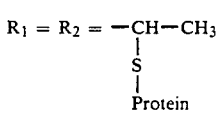

$R_3 = -CH_3$

[See also Granick, S. and D. Mauzerall, in *Metabolic Pathways*, Vol. 2 (D. M. Greenberg, ed.)(Academic Press, NY, 1961), pp. 525-616.]Protoheme and hemes a and c are prosthetic groups of all cytochromes in plant and animal cells.

It has now been discovered that insects can be killed by administration of a composition comprising one or more compounds selected from the group consisting of ALA, inducers of ALA in insects, and enhancers of ALA conversion to tetrapyrroles in insects.

In particular, it has now been discovered that living insects can be induced by exposure to exogenous ALA to accumulate artificially high amounts of tetrapyrrole intermediates in excess of levels normally found in such insects, and that such induced artificially high levels are toxic to the insect. This is surprising, since insects normally synthesize cytochromes only at a rate sufficient to keep up with growth and repair, and it was not previously believed that this rate would be sufficient to allow accumulation of lethal amounts of such tetrapyrrole intermediates.

While the exact mechanism of toxicity is not known, it appears that the accumulated tetrapyrroles may act in one of two ways. In the light, it is believed that the accumulated tetrapyrroles photosensitize the formation of singlet oxygen, which is a very strong oxidant. The singlet oxygen rapidly oxidizes the lipoprotein components of the insect cellular membranes, thus setting in motion a highly destructive free-radical chain reaction, which can be summarized as follows (hv=photon of light; ¹Tet=tetrapyrrole in the singlet ground state;

$^3$Tet* = tetrapyrrole in the triplet excited state; $^3O_2$ = oxygen in the triplet ground state; $^1O_2$* = oxygen in the singlet excited state; UMLP = unsaturated membrane lipoproteins):

1) $^1Tet + h\nu \rightarrow {}^3Tet*$
2) $^3Tet* + {}^3O_2 \rightarrow {}^1Tet + {}^1O_2*$
3) $^1O_2* + UMLP \rightarrow$ hydroperoxides
4) hydroperoxides → free radicals
5) free radicals + UMLP → more hydroperoxides
6) repetition of steps (4) and (5) until most of the UMLP are oxidized Photosensitization by injected tetrapyrroles has been described in animals and human tissues [see, e.g., Ellefson, R. D., Mayo Clinic Proc. 57:454-458 (1982); Christensen, T., T. Sandquist, K. Feren, H. Waksvik, and J. Moan, Br. J. Cancer 48:35-43 (1983); Hopf, F. R., and D. G. Whitten, in *The Porphyrins*, Vol. 1, Dolphin, D., ed. (Academic Press, New York, 1978), pp. 161-195; Sandeberg, S., I. Romslo, G. Hovding, and R. Bjorndal, Acta Dermatovener (Stockholm) Suppl. 100:75-80 (1982); Latham, P. S., and J. R. Bloomer, Photochem. Photobiol. 37:553-557 (1983); Bickers, D. R., R. Dixit, and H. Mukhtar, Biochim. Biophys. Res. Comm. 108:1032-1039 (1982)] but this phenomenon of ALA-dependent tetrapyrrole accumulation has not previously been demonstrated in insects, nor has it previously been adapted to kill undesirable insect species.

In the dark, it appears that accumulated tetrapyrroles act via a different mechanism and result in increased levels of Zn-protoporphyrin. Zn-Proto is not a natural metabolic intermediate of the porphyrin-heme pathway. Its occurrence in living cells and tissues usually denotes a poisoned porphyrin-heme metabolism [see, e.g., Lamolla, A. A., and T. Yamane, Science 186:936-938 (1974)]. Most ferrochelatases (the enzymes that insert ferrous iron into Proto to form heme) can insert Zn instead of iron into Proto to yield Zn-Proto, particularly under unfavorable reaction conditions [Marks, G. S., in Heme and Chlorophyll (Van Nostrand, 1969), pp. 146-147. While the exact mechanism is not known and Applicants do not wish to be bound by any particular theory, at present it is believed that the accumulation of Zn-Proto as a result of the insecticidal methods of the present invention may be caused by damage to the ferrochelatase system causing the enzyme to insert zinc instead of ferrous iron into some of the Proto. Eventually this means that zinc instead of ferrous iron is found in some of the prosthetic groups of the crucial respiratory enzyme cytochrome c oxidase. As a consequence those cytochrome c oxidase molecules containing Zn-Proto instead of heme can not hold tight to poisonous free radicals such as oxygen superoxides and hydroxide free radicals which are normally formed during the Krebs citric acid cycle [Halliwell, B., What's New in Plant Physiology 15:21-24 (1984)]. Under these circumstances the destructive free radicals may be released in the biological membrane environment and contribute to the free radical-dependent damage which results in insect death.

It has further been discovered that in addition to exposure to exogenous ALA, exposure of living insects to inducers of ALA will also result in accumulation of massive amounts of toxic tetrapyrroles in the insect tissues. By "inducer of ALA" or "inducer" is meant a compound which, when applied to insects, stimulates the insect to produce a higher-than-normal amount of endogenous ALA, which then has the same effect as exogenous ALA described above. Thus, the insecticidal compositions of this invention may comprise one or more inducers of ALA in addition to, or in lieu of, ALA itself. Non-limiting examples of inducers are 2,2'-dipyridyl; 1,10-phenanthroline; 4,7-dimethyl-1,10-phenanthroline; 4-methyl-1,10-phenanthroline; 5-nitro-1,10-phenanthroline; 5-methyl-1,10-phenanthroline; 5,6-dimethyl-1,10-phenanthroline; 4,7-diphenyl-1,10-phenanthroline; 5-chloro-1,10-phenanthroline; 3,4,7,8-tetramethyl-1,10-phenanthroline; 2,2'-dithiobis(pyridine N-oxide); 4,4'-dimethyl-2,2'-dipyridyl; phenyl 2-pyridyl ketoxime; and 2,2',6',2''-terpyridine.

It has further been discovered that certain compounds function as enhancers of ALA conversion to tetrapyrroles in insects. By "enhancer of ALA" or "enhancer" is meant a compound which when applied to insects enhances the capability of the treated insect to convert exogenous or endogenous ALA to insecticidal tetrapyrroles. Thus the insecticidal compositions of the present invention may also comprise one or more enhancers of ALA in addition to, or in lieu of, exogenous ALA or inducers of ALA. Non-limiting examples of suitable enhancers are 2,2'-dipyridyl; 1,10-phenanthroline; 4,7-dimethyl-1,10-phenanthroline; 4-methyl-1,10-phenanthroline; 5-nitro-1,10-phenanthroline; 5-methyl-1,10-phenanthroline; 5,6-dimethyl-1,10-phenanthroline; 4,7-diphenyl-1,10-phenanthroline; 5-chloro-1,10-phenanthroline; 3,4,7,8-tetramethyl-1,10-phenanthroline; 2,2'-dithiobis(pyridine N-oxide); 4,4'-dimethyl-2,2'-dipyridyl; phenyl 2-pyridyl ketoxime; and 2,2',6',2''-terpyridine. Certain compounds which function as inducers in one composition may function as enhancers in another composition or at different concentrations. Alternatively, certain compounds (e.g. 2,2'-dipyridyl; 1,10-phenanthroline; 4,7-dimethyl-1,10-phenanthroline; 4-methyl-1,10-phenanthroline; 5-nitro-1,10-phenanthroline; 5-methyl-1,10-phenanthroline; 5,6-dimethyl-1,10-phenanthroline; 4,7-diphenyl-1,10-phenanthroline; 5-chloro-1,10-phenanthroline; 3,4,7,8-tetramethyl-1,10-phenanthroline; 2,2'-dithiobis(pyridine N-oxide); 4,4'-dimethyl-2,2'-dipyridyl; phenyl 2-pyridyl ketoxime; and 2,2':6',2''-terpyridine) may simultaneously function as inducers and enhancers.

The insecticidal compounds of the present invention may also comprise combinations of two or more compounds selected from the group consisting of ALA, inducers, and enhancers, e.g. ALA + one or more inducers, ALA + one or more enhancers, ALA + one or more inducers + one or more enhancers, one or more inducers + one or more enhancers; etc.

The composition may also contain one or more of the following: suitable carrier(s) [e.g. colloidal magnesium aluminum silicate, pumice, talc, or combinations thereof]; solvent(s) [e.g. water, 0.45 acetone:0.45 ethanol:0.1 Tween 80:9 water (v/v/v/v), 0.45 acetone:0.45 methanol:0.1 Tween 80:9 water (v/v/v/v), 0.1-1% Tween 80 in water (v/v), 0.9 polyethylene glycol (PEG):0.1 Tween 80:9 water (v/v/v), 0.1-0.7 PEG:0.2-0.8 methanol:0.1 Tween 80:9 water (v/v/v/v), 0.9 methanol:0.1 Tween 80:9 water (v/v/v), 0.45 acetone:0.45 ethanol:0.2 Tween 80:0.9 ethylene glycol:18 water (v/v/v/v), or one or more of the following: benzene, toluene, xylene, kerosene, 2-methoxyethanol, propylene glycol, diethylene glycol, diethylene glycol diethyl ether, formamide, methylformamide, cyclohexanone, isophorone]; buffer(s) [e.g. citric acid]; wetting agent(s) [e.g. sodium N-methyl-N-oleoyltaurate, an alkylphenoxy polyoxyethylene ethanol, sodium alpha-olefin sulfonate, sodium isopropylnaphthalene sulfonate, polyoxyethylated vegetable oil]; dispersing agent(s) [e.g. sodium lignin sulfonate, the sodium salt of a naphthalene sulfonic acid-formaldehyde condensate, hydroxyethyl cellulose]; defoaming agent(s) [e.g. silicone]; emetic(s) [e.g. sodium tripolyphosphate, tetrapotassium pyrophosphate, arecotine, apomorphine, copper sulfate]; stench(es) [e.g. pyridine]; penetrant(s); surfactant(s); emulsifier(s); adjuvant(s); herbicide(s); and one or more other known insecticides.

The composition may be formulated in any manner conventionally used for insecticidal preparations, e.g. as an ingredient in the insect diet for internal systemic application, or as a solution, suspension, emulsion, flowable concentrate, emulsifiable concentrate, gel, paste, foam, cream, aerosol, wettable powder, dust, dispersable granules and the like for external topical application, according to procedures known to those skilled in the art. The formulation is constructed to deliver a suitable amount of one or more active ingredients to the target insect(s). For topical application, the composition is preferably a solution, suspension, emulsion, aerosol, flowable or emulsifiable concentrate, or wettable powder. Of course, the topical formulation must be such that the active ingredient(s) penetrate(s) the insect tissue and translocates to the sites of tetrapyrrole synthesis.

Where the active ingredient is combined with one or more active or inert compounds or compositions mentioned above, the combination may be done at ambient temperature, or at temperatures above or below ambient provided the stability of the final composition is not affected. Where the composition comprises ALA, the temperature is preferably kept between about 4° C. and about 75° C. When the insecticidal composition of the present invention is in aqueous solution, the pH can be at the isolectric point of the active ingredient(s), or above or below the isoelectric point, provided that the stability and solubility of the active ingredient is not so adversely affected as to interfere with efficacy. However, when the insecticidal composition comprises ALA, the pH is preferably adjusted so as to be between about pH 3 and about pH 8.

Where two or more components are combined to form the insectidical compositions, they are preferably combined under conditions assuring a uniform concentration throughout the mixture. This is conveniently done by techniques such as stirring, agitating, mixing, blending, etc.

In those cases where the active ingredient is be the sole component of the insecticidal composition of the present invention, the active ingredient must be carefully prepared to achieve uniform application. In the case of a solid active ingredient, this is conveniently done by subdividing into a fine powder. When such sole component is in the form of a liquid, it can conveniently be atomized to a fine mist or fog at suitable temperatures by techniques well known to those in the art. When the dietary or topical compositions are made in solution they may conveniently comprise concentrations of from about 2 to about 50 mM ALA and from about 0.1 to about 50 mM inducer or enhancer.

According to the methods of the present invention, the insects to be killed are contacted with an insecticidal composition comprising ALA and/or inducers of ALA and/or enhancers of ALA conversion to tetrapyrroles. The insecticidal compositions of the present invention may be applied topically, e.g. as a dust, soak, dip, spray, mist, or fog, in an amount sufficient to achieve lethal internal levels of tetrapyrroles. The amount of insecticidal composition to be applied topically will vary, depending on the particular active ingredient(s) selected, but in general will be an amount sufficient to supply from about 0.25–2 lb ALA per acre and/or from about 0.1–1.5 lb inducer or enhancer per acre. Means of determining optimum application rates are within the purview of those skilled in the art.

Alternatively, the insecticidal compositions of the present invention may be administered via the diet, incorporated in bait or other food or drink to be ingested by the insects to be killed. Again, the amount of insecticidal composition to be administered will vary, depending on the particular active ingredient(s) selected, but in general will be an amount sufficient to supply from about 10 ng to about 5 ug ALA per mg body weight, and/or from about 1 ng to about 5 ug of an inducer or enhancer per mg body weight.

If it is desired that the insect be killed via the dark mechanism, the insect may be treated and then shielded from exposure to light to allow maximum tetrapyrrole accumulation. The insect can be shielded in any convenient manner, as by covering the ground or area in which the insect is to be found with cloth, dark paper, or foil. Under field conditions, the ideal method to provide a period of dark incubation is to apply the insecticidal composition at dusk or during the night, at a time chosen to allow the insects to rest in the dark for at least one hour. It is to be understood that in order to facilitate tetrapyrrole accumulation, the dark need not be total absence of light, but rather substantial absence of light at wavelengths of from 380 to 700 nm. Preferably, the insects are kept in the dark for from about 1 to about 20 hours. One to 8 hours is particularly preferred. Of course, many insects naturally prefer dark environments and no extra steps need be taken to shield them from light after contact with the insecticidal composition.

If the insects are to be killed via the light mechanism, the insecticidal composition is applied or administered and the insects are concurrently or subsequently exposed to about 5 ft. candles or more of light at wavelengths of about 380 to about 700 nm. The light may be supplied by any convenient source, e.g. an incandescent lamp, metal halide lamp, sunlamp, or a cool white or skylight fluorescent bulb. In the field, of course, the preferred source of light is sunlight. The insects are exposed to light for a period of time sufficient to oxidize most of the unsaturated membrane lipoproteins; a period of from about 2 min to about 3 days is preferred.

The insects to be treated by the present invention can suitably be in the oval, larval, or adult stage. In larvae, the stage of the instar can affect susceptibility to treatment; larvae in later instars are relatively more susceptible to treatment than larvae in the earlier or middle instars. Accordingly, it may be necessary to vary the dosage levels according to the stage of development of the majority of the targeted larval population.

Insecticidal activity is indicated by alteration of the color of the skin, followed by desiccation and death.

A further understanding of this invention can be had from the following non-limiting examples. As used hereinabove and below unless expressly stated to the contrary, all temperatures and temperature ranges refer to the centigrade system and the terms ambient and room temperature refer to about 20°–25° C. The term percent or (%) refers to weight percent and the terms mole and moles refer to gram moles. "Level of significance" refers to the probability that for a population for which the correlation coefficient (r) is equal to zero, a sample of size n can be taken, for which the correlation coefficient equals or exceeds the calculated value of r reported for the given sample. The abbreviation "n.s." stands for "not significant".

EXAMPLE I

Pigments of the Diets on Which T. ni Larvae Were Reared

Eggs of *Trichoplusia ni* (Hubner) (cabbage looper, the most extensive pest in vegetable crops in the U.S.) were obtained from Ms. Paula Peters of the USDA Insect Biological Control Laboratory, Department of Entomology at the University of Missouri at Columbia. The larvae, pupae, and adult moths were reared in Percival Model I-60 incubators (Percival Mfg. Co., Boone, Iowa 50036) at 25° C. and 75% relative humidity with a daily regime of 14 hr light and 10 hr darkness. The larvae were maintained on artificial diets following the methods described by Waldbauer, G. P., R. W. Cohen and S. Friedman, Great Lakes Entomol. (1984) Twenty-thirty larvae were reared in individual 8-oz paper containers with clear plastic lids purchased from Lily-Tulip, Inc. (Augusta, Ga.). To avoid genetic shifts in the colony, wild collections were added to the culture every summer. To minimize microbial diseases, eggs and pupae of each generation were surface-sterilized.

Since *T. ni* larvae reared on a diet containing yellowish-green alfalfa meal acquired a yellowish-green color, while *T. ni* larvae reared on a diet without alfalfa meal were visually lacking in pigmentation, the endogenous pigment content of the diet was investigated as a preliminary step to studying induction of tetrapyrroles by chemical treatment.

The yellowish-green color of the diet containing alfalfa meal was typical of the yellowish-green color of Pheos (Chls that have lost their Mg atom) and of Pheobides (Chlides that have lost their Mg atom). This was confirmed by 77° K. spectrofluorometric analysis. Gram quantities of the diet were homogenized in 6 ml acetone:0.1N $NH_4OH$ (9:1 v/v) and the resulting aqueous acetone extract containing various pigments was cleared of lipoproteins and cell debris by centrifugation at 39000 g for 10 min at 0° C. Apolar pigments such as Chls and Pheos were removed from the aqueous acetone solution by extraction with hexane. The more polar di- and monocarboxylic pigments such as Proto, Mg-Proto, PChlides, Chlides and Pheos remained in the hexane-extracted aqueous acetone fraction. A small aliquot of the hexane extract containing the chlorophyllous pigments was dried under nitrogen gas and the residue was redissolved in 80% acetone for the spectrofluorometric determination of the amounts of Chls and Pheos according to the method of Bazzaz, M. B. and C. A. Rebeiz, Photochem. Photobiol. (1979) 30:709.

Fluorescence spectra were recorded on a fully corrected photon-counting spectrofluorometer Model SLM 8000DS as described in Rebeiz, C. A., A. Montazer-Zouhoor, H. J. Hopen and S. M. Wu, Enzyme Microb. Technol. (1984) 6:390. Excitation was at 400, 420, and 440 nm. Absorption spectra were recorded at a slit width of 2 nm on an Aminco model DW-2 dual wavelength spectrophotometer (Travenol Laboratories Inc., Silver Springs, Md. 20910). Controls were MV Pheo a and b prepared from MV Chl a and b, respectively, as described in Bazzaz, M. B. and C. A. Rebeiz, Photochem. Photobiol. (1979) 30:709. Results are shown in Table I:

TABLE I

Spectrofluorometric Properties in Ether at 77° K. of the Predominant Pigments of the Alfalfa Meal-Containing Diet and of *T. ni* Reared on that Diet

| Experiment | # | Material | Fluorescence at 77° K. (nm) Red emission | Soret excitation | Pigment Identification |
|---|---|---|---|---|---|
| A | 1 | Authentic MV Pheo b | 656 | 440 > 450 | |
| B | 1 | Authentic MV Pheo a | 666 | 414 | |
| C | 1 | Apolar extract of diet | 655 | 440 > 450 | MV Pheo b |
|   | 2 |  | 666–667 | 414 | MV Pheo a |
|   | 3 | Polar extract of diet | 654–655 | 440 > 450 | MV Pheobide b |
|   | 4 |  | 666–667 | 414–415 | MV Pheobide a |
| E | 1 | Polar extract of T.ni | 655 | 440 > 450 | MV Pheobide b |
|   |   |  | 666–667 | 414 | MV Pheobide a |

Successive excitations of the ether glass of the apolar extract between 400 and 450 nm elicited two Chl-like emission bands with maxima at 655 and 666–667 nm respectively (Table I: C 1, 2). The Soret excitation spectrum of the 655 nm emission band exhibited split Soret excitation maxima at 440 nm (large maximum) and at 450 nm (smaller maximum) (Table I: C 1). These emission and excitation maxima were identical to those of authentic MV Pheo (E440>E450F656) (Table I: A). In this context "E440>450" to the split Soret excitation maxima of MV Pheo b at 77° K. in ether, while "F656" refers to the fluorescence emission maximum of MV Pheo b at 656 nm. The (E440>E450F656) fluorescent band was therefore identified as MV Pheo b. Small amounts of MV Chl b were also present.

The Soret excitation spectrum of the 666 nm emission band, exhibited a single excitation maximum at 414 nm, and was identical to authentic MV Pheo a (Table I: B, C 2). This (E414F666) fluorescent compound was therefore identified as MV Pheo a.

The spectrofluorometric properties of the polar fraction were very similar to those of the apolar fraction (Table I:C 1–4). However, the (E440>E450F655) and (E414F666-667) compounds were too polar to partition with hexane and remained in the aqueous acetone residue. They were identified with MV Pheobide b and MV Pheobide respectively. Pheobides have the same electronic spectroscopic properties as Pheos but are more polar because they have lost the long chain alcohol at position 7 of the macrocycle. It has been documented that the extent of esterification at positions 6 and 7 of the macrocycle has no effect on the electronic absorption and fluorescence properties of tetrapyrroles (see, e.g. Belanger, F. C. and C. A. Rebeiz, J. Biol. Chem. (1982) 257:1360).

The amounts of Proto, Mg-Protos, PChlides, Chlides and Pheobides were determined by spectrofluorometry on aliquots of the hexane-extracted acetone polar fraction according to the methods of Rebeiz, C. A., J. R. Mattheis, B. B. Smith, C. C. Rebeiz, and D. F. Dayton, Arch. Biochem. Biophys. (1975) 171:549 and Bazzaz, M. B. and C. A. Rebeiz, Photochem. Photobiol. (1979) 30:709. Results are shown in Table II:

TABLE II

Pigment Content of the Diets on which the Larvae were Reared

| Experiment | Diet | Proto | MV Chlide a | MV Chlide b | MV Pheobide a | MV Pheobide b | MV Chl a | MV Chl b | MV Pheo a | MV Pheo b |
|---|---|---|---|---|---|---|---|---|---|---|
| | | | | | | Pigment content in nmoles per 100 mg protein | | | | |
| A | Diet + A.M. | 0 | 2.39 | 5.45 | 53.28 | 108.07 | 0 | 3.71 | 31.52 | 49.54 |
| B | Diet − A.M. | 0 | 0 | 0 | 0 | 0 | 0.15 | 0.05 | 0.29 | 0.74 | wherein "Diet+A.M."=diet containing alfalfa meal, and "Diet−A.M."=diet lacking alfalfa meal.

The amounts of MV Pheobide and b in the alfalfa meal-containing diet is reported in Table II: A. Small amounts of Chlide a and b were also present (Table II: A). The diet that lacked alfalfa meal contained only trace amounts of chlorophyllous pigments (Table II: B).

EXAMPLE II

Pigments of T. ni

T. ni larvae in their fifth instar reared on diets containing or lacking alfalfa meal were thoroughly homogenized either with mortar and pestle or with a Brinkman model PT 10/35 homogenizer (Brinkman Instrument Co., Westbury, N.Y. 11590) in acetone: 0.1N NH$_4$OH (9:1 v/v) at a rate of 6 ml of solvent per gram of tissue. Polar and apolar pigments were extracted as in Example I. Results are shown in Table III:

TABLE III

Pigment of T. ni Larvae

| Experiment | Diet | Proto | MV Chlide a | MV Chlide b | MV Pheobide a | MV Pheobide b | MV Chl a | MV Chl b | MV Pheo a | MV Pheo b |
|---|---|---|---|---|---|---|---|---|---|---|
| | | | | | | Pigment content in nmoles per 100 mg protein | | | | |
| A | T. ni + A.M. | 0 | 0.68 | 12.31 | 21.39 | 45.99 | 0.12 | 0.21 | 0.04 | 1.56 |
| B | T. ni − A.M. | 0.2 | 0.14 | 0.25 | 0.04 | 1.88 | 0.27 | 0.07 | 0.07 | 0 | wherein "T. ni+A.M.=larvae reared on diet containing alfalfa meal and "T. ni−A.M."=larvae reared on diet lacking alfalfa meal.

In contrast to the alfalfa meal diet which contained substantial amounts of MV Pheo a and b in addition to MV Pheobide and T. ni contained smaller amounts of Pheos, the level of which appeared to vary from cohort to cohort (Table III: A; see also Table IV below). The pigments accumulated by the larvae were more polar and consisted mainly of MV pheophorbide and MV pheophorbide (Table I: E; Table III: A). On the other hand, larvae reared on the diet that lacked alfalfa meal contained only trace amounts of chlorophyllous pigments (Table III: B).

In order to determine the site of pigment accumulation, the skin, hemolymph and gut of fifth instar T. ni larvae reared on the alfalfa meal-containing diet were separated and analyzed for pigment content. Hemolymph was collected from 9 to 10 larvae fed a diet without alfalfa and from 9 to 10 larvae fed a diet with alfalfa by gently piercing the skin over the chambered heart at one posterior segment of the larvae's abdomen. The extruded hemolymph was collected in a No. 22 syringe and was immediately squirted into cold acetone: 0.1N NH$_4$OH (9:1 v/v). After collecting the hemolymph, the larvae were frozen in liquid nitrogen, then were partially thawed before slitting the skin longitudinally with a sharp scalpel. The thawed skin (i.e. the insect integument) was then carefully peeled away from the still frozen guts. The skin was placed in ice-cold distilled water for further washing while the guts were placed in ice-cold acetone: 0.1N NH$_4$OH (9:1 v/v). The skin was rinsed three times with distilled water, then was placed in cold acetone: 0.1N NH$_4$OH (9:1 v/v) for homogenization. The hemolymph, gut and integument fractions were homogenized in cold acetone: 0.1N NH$_4$OH (9:1 v/v) with mortar and pestle and extracted according to the procedure of Example I. Results are shown in Table IV:

TABLE IV

Pigment Content of Various Tissues of T. ni Larvae Reared on an Alfalfa Meal-Containing Diet

| | Proto | MV Chlide a | MV Chlide b | MV Pheobide a | MV Pheobide b | MV Chl a | MV Chl b | MV Pheo a | MV Pheo b |
|---|---|---|---|---|---|---|---|---|---|
| | | | | Pigment content in nmoles per 100 mg protein | | | | | |
| skin | 0 | 0.05 | 0.12 | 0.42 | 1.03 | 0.13 | 0.05 | 0.07 | 0.08 |
| gut | 0 | 0.39 | 2.61 | 12.22 | 18.05 | 0.38 | 0.49 | 9.75 | 17.32 |
| hemolymph | 0.07 | 0.25 | 0.13 | 0.18 | 1.19 | 0.98 | 0.50 | 0.18 | 0 |

As reported in Table IV, most of the pigment was found in the gut. Small amounts of pigment were also detected in the integument and in the hemolymph.

EXAMPLE III

Protoporphyrin IX Accumulation in T. ni Treated With Delta-aminolevulinic Acid and 2,2'-Dipyridyl A block of food (2.5×1.5×1 cm) and 20 to 30 T. ni larvae in their third instar were placed in an 8-oz paper container (9 cm in diameter) and the container was sprayed with 0.35 ml of 40 mM ALA+30 mM 2,2'-DP in acetone: ethyl alcohol: Tween 80: water (0.45:0.45:0.1:9 v/v/v/v), adjusted to pH 3.5. The solution was applied as a fine spray at an average droplet diameter of about 50 microns. This was equivalent to a spray rate of 40 gallons per acre. Treatments were replicated four times. The sprayed containers were covered with a transparent plastic lid and the treated larvae were then incubated overnight (17 hr, generally from 4 pm on a particular day to 9 am the next day) in darkness at 28° C. before extraction as in Example II. Results are shown in Table V:

DV Mg-Proto (Table V). Altogether these results indicated that treatment of *T. ni* larvae with ALA and

TABLE V

Absorbance and Fluorescence Properties of the Predominant Pigment that Accumulates in *T. ni* after Treatment with ALA + 2,2'-DP

| Material | Absorbance at 298° K. in 80% acetone (nm) | Fluorescence at 77° K. in ether (nm) Red emission | Fluorescence at 77° K. in ether (nm) Soret excitation | Pigment identification |
|---|---|---|---|---|
| Authentic Uro | 400, 498, 531, 568, 622 | 618 | 402 | |
| Authentic Copro | 405, 496, 528, 565, 619 | 619 | 400 | |
| Authentic Proto | 403, 503, 538, 573, 629 | 629 | 409 | |
| Authentic Mg-Proto | 417, 553, 592 | 591 | 424 | |
| *T. ni* extract | 403, 503, 538, 573, 629 | 629 | 409 | DV Proto IX |
| *T. ni* extract after Mg-insertion | | 591 | 424 | DV Mg-Proto IX |

Although the pigment profile of the control larvae, which were sprayed with solvent only, was similar to that described in Tables I: E and III: A, the pigment profile of the ALA+2,2'-DP-treated larvae was drastically different. The fluorescence of MV Pheobide and in the hexane-extracted aqueous acetone fraction became completely obscured by fluorescence with an emission maximum at room temperature at 631 nm and a Soret excitation maximum at 405 nm. This fluorescence profile was identical to that of authentic DV Proto dissolved in hexane-extracted aqueous acetone [FIG. 1: (a) hexane-extracted acetone extract of control larvae; the emission peak at 674 nm is that of MV Pheo a; (b) extract of treated larvae; (c) authentic DV Proto in hexane-extracted acetone]. Confirmation of the nature of the accumulated pigment was achieved by comparing its absorption spectrum in 80% acetone to those of uroporphyrin octamethyl ester, coproporphyrin, DV Proto, and DV Mg-Proto (Porphyrin Products, Logan, Utah). As shown in Table V, the 80% acetone extract of *T. ni* exhibited an absorption spectrum at room temperature which was identical to authentic DV Proto. After transfer to ether, the pigment exhibited the same fluorescence emission and Soret excitation maxima at 77° K. (629 and 409 nm respectively) as authentic Proto. After insertion of Mg into the pigment (as described in Belanger, F. C. and C. A. Rebeiz, J. Biol. Chem. (1982) 257:1360), it exhibited the same fluorescence emission and excitation maxima in ether at 77° K. as authentic 2,2'-DP resulted in the biosynthesis and accumulation of DV Proto by the larvae.

EXAMPLE IV

Insecticidal effects of the ALA+2,2'-DP treatment

To determine relationships between the ALA+2,2'-DP treatment, pigment accumulation, and insecticidal effects, *T. ni* larvae in the third instar were sprayed with 40 mM ALA+30 mM 2,2'-DP at a pH of 3.5, and were incubated overnight (17 hr) in darkness at 28° C. as in Example III. The next morning, a set of three replicates was placed in the greenhouse at 25° C. under a 14-hr light, 10-hr dark photoperiod, in order to observe larval death. The fourth replicate constituted the control (sprayed with solvent only); the control and treated replicates were extracted for quantitative pigment determinations as in Example II. Larval death was assessed by daily comparison of larval survival among the treated and control insects. Protein was determined by suspending the acetone-insoluble residue which was precipitated by centrifugation of the tissue homogenate in distilled water with an all- glass tissue grinder. Total proteins were determined by biuret on a small aliquot of the suspension after delipidation according to the method of Rebeiz, C. A. and P. A. Castelfranco, Plant Physiol. (1965) 40:281. The results of several experiments are reported in Table VI:

TABLE VI

Effect of ALA + 2,2'-DP on the Biosynthesis and Accumulation of Proto and on the Extent of Larval Death in *T. ni*

| Experiment | Treatment | Pigment content after 17 hr of dark incubation nmoles per 100 mg protein | | | | | | | | larval death (%) |
|---|---|---|---|---|---|---|---|---|---|---|
| | | Proto | MV Chlide a | MV Chlide b | MV Pheobide a | MV Pheobide b | MV Chl a | MV Chl b | MV Pheo a | MV Pheo b | |
| A | Control | 0.1 | 0.3 | 0.8 | 5.5 | 7.8 | 1.4 | 0.5 | 2.9 | 4.2 | 3 |
| | Treated | 85.0 | 0.0 | 0.0 | 0.0 | 0.0 | 0.4 | 0.1 | 0.6 | 1.7 | 80 |
| | Δ change | 84.9 | −0.3 | −0.8 | −5.5 | −7.8 | −1.0 | −0.4 | −2.3 | −3.5 | 77 |
| B | Control | 0.0 | 0.2 | 0.4 | 3.4 | 5.7 | 0.1 | 0.0 | 2.5 | 4.8 | 1 |
| | Treated | 96.7 | 0.0 | 0.0 | 0.0 | 0.0 | 0.5 | 0.4 | 1.3 | 4.4 | 75 |
| | Δ change | 96.7 | −0.2 | 0.0 | −3.4 | −5.7 | −0.5 | 0.4 | −1.2 | −0.4 | 74 |
| C | Control | 0.1 | 0.4 | 1.1 | 12.1 | 29.0 | 0.3 | 0.1 | 2.1 | 4.1 | 13 |
| | Treated | 12.8 | 0.3 | 0.3 | 5.1 | 9.5 | 1.9 | 1.3 | 2.0 | 7.4 | 47 |
| | Δ change | 12.7 | −0.1 | −0.8 | −7.0 | −19.5 | −1.6 | −1.2 | −0.1 | −3.3 | 34 |
| D | Control | 0.1 | 1.0 | 2.5 | 14.4 | 23.9 | 1.5 | 2.3 | 6.2 | 2.3 | 6 |
| | Treated | 89.7 | 0.2 | 2.4 | 11.3 | 23.5 | 6.6 | 3.4 | 3.6 | 3.4 | 89 |
| | Δ change | 89.6 | −0.8 | −0.1 | −3.1 | −0.4 | 5.6 | 1.1 | 3.4 | 1.1 | 83 |
| Correlation (r) between pigment content and larval death | | 0.945 | −0.6 | −0.13 | −0.36 | −0.27 | 0.46 | 0.31 | −0.43 | −0.15 | |
| Level of | | 0.1% | n.s. | n.s. | n.s. | n.s. | n.s. | n.s. | n.s. | n.s. | |

TABLE VI-continued

Effect of ALA + 2,2'-DP on the Biosynthesis and Accumulation of Proto and on the Extent of Larval Death in *T. ni*

| Experiment | Treatment | Proto | MV Chlide a | MV Chlide b | MV Pheobide a | MV Pheobide b | MV Chl a | MV Chl b | MV Pheo a | MV Pheo b | larval death (%) |
|---|---|---|---|---|---|---|---|---|---|---|---|
| significance | | | | | | | | | | | |

Pigment content after 17 hr of dark incubation. nmoles per 100 mg protein wherein "Larval death" refers to percent death at the beginning of the fourth photoperiod, i.e. after 3 days in the greenhouse, and "Δ change" refers to the difference in pigment content between the ALA+2,2'-DP-treated larvae and the control larvae after the 17-hour post-spray dark incubation period.

The ALA+2,2'-DP treatment resulted in massive Proto accumulation and significant larval death. Percent larval death exhibited a high degree of correlation with Proto accumulation (Table VI). Most of the death occurred during the first photoperiod. Within minutes to a few hours after exposure to light the larvae became sluggish and flaccid due to the loss of body fluids; death was accompanied by extensive desiccation.

To determine the site of Proto accumulation the integument, hemolymph and gut of ALA+2,2'-DP-treated larvae, in their early fifth instar, were separated and analyzed for pigment content as in Example II. On a per unit protein basis, about 59% of the accumulated Proto was observed in the hemolymph, 35% in the gut and 6% in the integument.

EXAMPLE V

Effects of Protoporphyrin Accumulation on Larval Death and Bodyweight Change in Darkness and in Light During the course of experimentation, it was observed that the ALA+2,2'-DP treatment was consistently causing larval death in darkness as well as in the light. To determine whether the ALA+2,2'-DP-dependent larval death was a photodynamic phenomenon or not, *T. ni* larvae in the third instar were sprayed either with solvent only (controls) or with 40 mM ALA+30 mM 2,2'-DP adjusted to pH 3.5 as in Example III. The sprayed larvae were allowed to accumulate Proto overnight by incubation in darkness for 17 hr at 28° C. The next morning, some of the larvae were exposed to 0, 3, or 6 hr of light in the greenhouse, before pigment extraction as in Example II. Duplicate samples subjected to the same light treatment were returned to darkness for 48, 45, and 42 hr respectively, before monitoring average larval death as in Example V. Further evaluation of treatment-dependent damage among surviving larvae was by determination of body weight after 3 days of photoperiodic exposure in the greenhouse. The results of two experiments are reported in Table VII:

TABLE VII

Effect of Proto Accumulation on *T. ni* Larval Death and Body Weight Change in Darkness and in Light

| Experiment | # | Light/Dark regime, after spraying and 17 hr dark incubation | Proto content after 17 hr post-spray dark incubation and 0-6 hr illumination (nmol/100 mg protein) | Post-spray larval death after 17 hr dark incubation (%) | Post-spray larval death after total 65 hr period (%) | Post-treatment body weight per live larva after the total 65-hr period (mg) |
|---|---|---|---|---|---|---|
| A | 1 | Control, two 14-hr light + 10-hr dark photoperiods | 0.2$^a$ | 1 | 12 | 45.1 |
| A | 2 | Treated, 0 hr light + 48 hr dark | 62.0$^a$ | 28 | 31 | 44.5 |
| A | 3 | Treated, 3 hr light + 45 hr dark | 0.4$^b$ | 21 | 60 | 43.4 |
| A | 4 | Treated, 6 hr light + 42 hr dark | 1.1$^c$ | 22 | 73 | 26.6 |
| A | 5 | Treated, two 14-hr light + 10-hr dark photoperiods | 62.0$^a$ | 19 | 80 | 16.6 |
| B | 1 | Control, two 14-hr light + 10-hr dark photoperiods | 0.2$^a$ | 0 | 22 | 44.1 |
| B | 2 | Treated, 0 hr light + 48 hr dark | 40.1$^a$ | 19 | 48 | 45.7 |
| B | 3 | Treated, 3 hr light + 45 hr dark | 1.2$^b$ | 20 | 65 | 32.1 |
| B | 4 | Treated, 6 hr light + 42 hr dark | 0.6$^c$ | 21 | 77 | 20.5 |
| B | 5 | Treated, two 14-hr light + 10-hr dark photoperiods | 40.1$^a$ | 22 | 95 | 3.6 |
| Correlation coefficient | | | | | 0.808$^d$ | −0.851$^e$ |

TABLE VII-continued

Effect of Proto Accumulation on *T. ni* Larval Death and Body Weight Change in Darkness and in Light

| Experiment # | Light/Dark regime, after spraying and 17 hr dark incubation | Proto content after 17 hr post-spray dark incubation and 0-6 hr illumination (nmol/100 mg protein) | Post-spray larval death after | | Post-treatment body weight per live larva after the total 65-hr period (mg) |
|---|---|---|---|---|---|
| | | | 17 hr dark incubation (%) | total 65 hr period (%) | |
| level of significance | | | 5% | | 1% |

*Proto content after the post-spray 17 hr dark-incubation period
[b]Proto content after the post-spray 17 hr dark-incubation period and 3 hr of illumination
[c]Proto content after the post-spray 17 hr dark-incubation period and 6 hr of illumination
[d]Correlation between larval death and the extent of post-spray exposure to light. In computing the correlation coefficient, the larval death of the control was subtracted from that of the treated
[e]Correlation between the extent of post-spray exposure to light and average body weight change per surviving larva. In calculating the correlation coefficient, the average body weight of the control larvae was subtracted from that of the treated larvae.

Treatment of the larvae with ALA+2,2'-DP resulted in the accumulation of Proto. A significant degree of larval death was also observed in the treated larvae at the end of the 17-hr post-spray dark incubation period, before any exposure to light (Table VII: A 2, B 2). Additional dark incubation resulted in further larval death. This mode of larval death is herein referred to as dark-dependent larval death. The larvae that survived the dark-larval death period did not undergo a detectable body weight loss (Tables VII: A 1, 2; B 1, 2). These results indicated that the ALA+2,2'-DP-dependent Proto accumulation was accompanied by larval death in darkness.

Three or 6 hours of illumination of the larvae that had accumulated Proto during the 17-hr post-spray dark-incubation resulted in the destruction and disappearance of the accumulated Proto (Table VII: A 2-4, B 2-4). Mortality of treated larvae that were exposed to 3 or 6 hr of illumination before being placed back in darkness for 45 and 42 hr, respectively, exceeded the level of dark-larval mortality (Table VII: A 2-4, B 2-4). This mode of larval death is herein referred to as light-dependent larval death. This form of mortality exhibited a significant correlation with the length of illumination (Table VII: column 6). Furthermore, the treated larvae that survived the light treatment exhibited a significant inhibition in bodyweight gain as compared to the untreated controls which were sprayed with solvent only (Table VII, column 7). The correlation between the length of the post-treatment exposure to light and inhibition in body weight gain was highly significant (Table VII, column 7).

Altogether these results indicated that in addition to dark-larval death, Proto accumulation resulted in a light-dependent or photodynamic larval mortality. Furthermore the accumulated Proto disappeared during illumination, probably as a consequence of photodestruction.

EXAMPLE VI

Synergistic Effects of ALA and 2,2'-DP on Proto Accumulation and Larval Death in *T. ni*

The relative effects of ALA and 2,2'-DP on Proto accumulation and larval death in third instar *T. ni* treated as in Example III and assayed as in Example II are described in Table VIII: A:

TABLE VIII

Synergistic Effects of ALA and 2,2'-DP in Causing Proto Accumulation and Larval Death in *T. ni*

| Experiment | # | Treatment | Proto content (nmol/100 mg protein) | Larval death after 3 days in the greenhouse (%) |
|---|---|---|---|---|
| A | 1 | Control | 0 | 6 |
| | 2 | 40 mM ALA | 2.5 | 26 |
| | 3 | 30 mM 2,2'-DP | 15.5 | 41 |
| | 4 | 40 mM ALA + 30 mM 2,2'-DP | 80.4 | 90 |
| B | 1 | Control | 0 | 2 |
| | 2 | 30 mM 2,2'-DP | 11 | 61 |
| | 3 | 30 mM 2,2'-DP + 10 mM ALA | 75 | 86 |
| | 4 | 30 mM 2,2'-DP + 20 mM ALA | 89 | 76 |
| | 5 | 30 mM 2,2'-DP + 40 mM ALA | 73 | 92 |
| C | 1 | Control | 0 | 7 |
| | 2 | 15 mM 2,2'-DP | 1 | 22 |
| | 3 | 15 mM 2,2'-DP + 10 mM ALA | 8 | 42 |
| | 4 | 15 mM 2,2'-DP + 20 mM ALA | 34 | 40 |
| | 5 | 15 mM 2,2'-DP + 40 mM ALA | 27 | 43 |
| D | 1 | Control | 0.2 | 5 |
| | 2 | 40 mM ALA | 1.1 | 7 |
| | 3 | 40 mM ALA + 5 mM 2,2'-DP | 3.8 | 4 |
| | 4 | 40 mM ALA + 10 mM 2,2'-DP | 6.7 | 18 |
| | 5 | 40 mM ALA + 20 mM 2,2'-DP | 12.1 | 34 |
| | 6 | 40 mM ALA + 30 mM 2,2'-DP | 15.3 | 71 |
| Correlation between Proto content and larval death | | | 0.857 | |
| Level of significance | | | 0.1% | |

Delta-aminolevulinic acid alone resulted in a modest level of Proto accumulation and larval death (Table VIII: A 2). 2,2'-Dipyridyl in the absence of added ALA was more effective than ALA in causing Proto accumulation and larval death (Table VIII: A 2, 3); i.e., in the absence of added ALA, 2,2'-DP acted as an inducer of Proto accumulation. Finally, the synergistic effects of ALA+2,2'-DP were manifested when the two chemicals were used jointly in treating the *T. ni* larvae. Under these conditions Proto accumulation (80.4 nmoles) and larval death (90%) far exceeded the sum of Proto accumulation (2.5+15.5=18 nmoles) and larval death (26+41=67%) caused by the separate ALA and 2,2'-DP treatments (Table VIII: A 2-4).

EXAMPLE VII

Enhancement of ALA Conversion to Protoporphyrin by 2,2'-Dipyridyl

To determine whether in addition to its inducing properties (Table VIII: A 3) 2,2'-DP exhibited enhancing properties as suggested by Table VIII: A, its effects on Proto accumulation and on concomitant larval death was examined in the presence of various amounts of added ALA. Larvae in their third instar were sprayed as in Example III and assayed as in Example II. At high (30 mM) and medium (15 mM) concentration, 2,2'-DP exhibited enhancing properties in addition to its Proto-inducing properties. The Proto-inducing properties of 2,2'-DP were demonstrated by the increase in Proto accumulation and the concomitant larval death in the absence of added ALA (Table VIII: B 2, C 2). The enhancing properties of 2,2'-DP were evidenced by the dramatic increase in Proto accumulation and larval death in the ALA+2,2'-DP-treated larvae, over and beyond those treated with 2,2'-DP alone, as a result of the greatly improved conversion of exogenous ALA to Proto (Table VIII: B 3-5, C 3-5). Finally the dependence of the 2,2'-DP enhancing properties upon 2,2'-DP concentration is described in Table VIII: D.

Altogether the foregoing results indicate that although in the absence of added ALA, 2,2'-DP acted as an inducer of Proto accumulation, in the presence of exogenous ALA it also acted as an enhancer of ALA conversion to Proto. 2,2'-DP is thus an example of an inducer-enhancer of tetrapyrrole biosynthesis.

EXAMPLE VIII

Effect of pH on ALA+2,2'-DP Dependent Proto Accumulation and on Larval Death in *T. ni*

Delta-aminolevulinic acid is a Zwitterion, i.e. its net charge is a function of pH. Since its isoionic point is at pH 6.47, it acquires a positive charge below pH 6.47 and a negative charge above that pH. Since the translocation of Zwitterions into biological tissues is influenced by the magnitude of the net electrical charge on the ion, the influence of this parameter on the translocation of ALA and 2,2'-DP into the treated larvae was examined. The extent of translocation of ALA and 2,2'-DP into the *T. ni* larvae was inferred from the extent of Proto

*T. ni* larvae in the third instar were sprayed with 30 mM 2,2'-DP+40 mM ALA solutions at pH 3.5 and 5.5 (ALA positively charged) and at pH 7.5 (ALA negatively charged) according to the procedure of Example III. As usual controls were sprayed with solvent only. After the 17-hr post-spray dark-incubation period, some of the larvae were extracted for Proto determination according to the procedure of Example II, while duplicate samples were exposed to light in the greenhouse. Larval death was determined after 3 days in the greenhouse. Results are shown in Table IX:

TABLE IX

Effect of pH on ALA + 2,2'-DP Dependent Proto Accumulation in *T. ni* Larvae

| Experiment | # | Treatment | Proto content (nmol/ 100 mg protein) | Larval death after 3 days in the greenhouse (%) |
|---|---|---|---|---|
| A | 1 | Control | 0.1 | 3 |
|   | 2 | Treated, pH 3.5 | 85.0 | 81 |
|   | 3 | Treated, pH 5.5 | 73.8 | 85 |
|   | 4 | Treated, pH 7.5 | 108.5 | 80 |
| B | 1 | Control | 0.0 | 1 |
|   | 2 | Treated, pH 3.5 | 96.7 | 75 |
|   | 3 | Treated, pH 5.5 | 110.4 | 82 |
|   | 4 | Treated, pH 7.5 | 73.7 | 85 |
| Correlation coefficient | | | 0.007[a] | 0.540[b] |
| Level of significance | | | n.s. | n.s. |

[a] Correlation between pH and Proto content in ALA + 2,2'-DP-treated larvae
[b] Correlation between pH and larval death in ALA + 2,2'-DP-treated larvae As shown in Table IX, considerable amounts of Proto were formed by the treated larvae at all pH values. Larval death was also substantial at all pH values. Between pH 3.5 and 7.5, neither Proto accumulation nor larval death appeared to be correlated to pH. Altogether these results indicate that translocation of ALA+2,2'-DP into *T. ni* larvae and subsequent conversion of ALA to Proto by the larvae were not strictly dependent on pH in the range 3.5 to 7.5.

EXAMPLE IX

Dependence of Larval Death in *T. ni* Treated with ALA+2,2'-DP on the Age of the Larvae The dependence of larval death in ALA+2,2-DP-treated *T. ni* on the age of the treated larvae was investigated. *T. ni* larvae, in the first, second, 30 mM 2,2'-DP at pH 3.5 as in Example III. After a 17-hr dark-incubation period, the treated and control larvae were exposed to light in the greenhouse. Larval death was evaluated after 3 days in the greenhouse. Results are shown in Table X:

TABLE X

Dependence of the Susceptibility of *T. ni* to the ALA + 2,2'-DP Treatment upon the Instar of the Treated Larvae

| Experiment | # | Instar[a] | Larval death over and beyond the controls after 3 days in the greenhouse (%) |
|---|---|---|---|
| A | 1 | 1 | 76 |
|   | 2 | 2 | 42 |
|   | 3 | 3 | 43 |
| B | 1 | 1 | 64 |
|   | 2 | 2 | 63 |
|   | 3 | 3 | 27 |
| C | 1 | 2 | 75 |
|   | 2 | 3 | 28 |
|   | 3 | 4 | 11 |
| D | 1 | 2 | 70 |
|   | 2 | 3 | 23 |
|   | 3 | 4 | 11 |
| Correlation coefficient between the rank of the instar and larval death | | | −0.897 |
| Level of significance | | | 0.1% |

[a] 1, 2, 3 refer to the first, second, and third instar respectively

Table X shows that the susceptibility of *T. ni* to the ALA+2,2'-DP treatment was inversely proportional to the rank of the instar, with young first instar larvae being the most susceptible and older fourth instars being the least susceptible.

To determine whether susceptibility to the ALA+2,2'-DP treatment depended on the stage of development within a particular instar, *T. ni* larvae in the early, mid- and late stages of third and fourth instars were treated with ALA+2,2'-DP as above. Results are shown in Table XI:

TABLE XI

Dependence of the Susceptibility of *T. ni* to ALA + 2,2'-DP upon the Stage of Development within a Particular Instar

| Experiment | # | Stage of the instar | Susceptibility ranking | Larval death over and beyond the controls after 3 days in the greenhouse | |
|---|---|---|---|---|---|
| | | | | before normalization (%) | after normalization (%) |
| A | 1 | Mid third | 1 | 47 | 52 |
| | 2 | Early third | 2 | 60 | 66 |
| | 3 | Late third | 3 | 91 | 100 |
| B | 1 | Mid third | 1 | 47 | 92 |
| | 2 | Early third | 2 | 39 | 76 |
| | 3 | Late third | 3 | 51 | 100 |
| C | 1 | Mid fourth | 1 | 21 | 57 |
| | 2 | Early fourth | 2 | 18 | 49 |
| | 3 | Late fourth | 3 | 27 | 100 |
| D | 1 | Mid fourth | 1 | 26 | 54 |
| | 2 | Early fourth | 2 | 35 | 73 |
| | 3 | Late fourth | 3 | 48 | 100 |
| Correlation between the stage of development within an instar and larval death | | | | 0.739 | |
| Level of significance | | | | 1% | |

The results suggest that, for a particular instar, the late stage was the most susceptible, followed by the early and mid stages respectively. This in turn suggested that the closer the larvae were to apolysis (separation of the cuticle from the epidermis), the more susceptible they were to the ALA+2,2'-DP treatment. The mid, early and late stages of every particular instar were assigned a rank of 1, 2, or 3, with "1" denoting the least susceptible stage and "1" denoting the most susceptible state. To eliminate statistical differences in susceptibility between third and fourth instars (see Table X), all percent death values within every experiment were normalized to the same value. The latter was chosen to be 100, and represented the percent death for the late stage within every instar (Table XI, last column). In this manner it became possible to test the relationship between larval death and the early, mid, and late stages of the instar, irrespective of the rank of the instar. As shown in Table XI, this relationship was highly significant with the early and mid stages of the instar being less susceptible to the ALA+2,2'-DP treatment than the late stage of the instar. This period of maximum susceptibility corresponds to the period when the larvae are quiescent and the new cuticle for the next instar is being actively synthesized beneath the old cuticle.

EXAMPLE X

Relationship between Larval Species, ALA+2,2'-DP Dependent Proto-accumulation, and Larval Death To determine whether ALA+2,2'-DP-dependent Proto accumulation and larval death were general phenomena common to all insect larvae or specific to certain particular insect species, a study of the response of various larval species to the ALA+2,2-DP treatment was undertaken.

Colonies of the corn borer *Heliothis zea* (Boddie) (Lepidoptera: Noctuidae) were grown from eggs provided by Dr. Gilbert Waldbauer, in the Department of Entomology at the University of Illinois at Urbana-Champaign. The larvae were fed the same diet as *T. ni* above.

The larvae of *H. zea* were sprayed as in Example III; however, unlike *T. ni*, the larvae of *H. zea* are cannibalistic and had to be treated differently. Twenty-five larvae 1 cm long (mixture of third and fourth instar) were placed singly with a cube of diet into individual compartments (3×5×1.5 cm) of a 25-celled plastic tray (Bioserve, Inc., Frenchtown, N.J. 08825). To confine the larvae to their individual compartments, the plastic tray was covered with a glass plate. The glass plate was removed before spraying and was placed back immediately thereafter. Spraying was as described for *T. ni*. The sprayed containers were covered with a glass plate before placing in darkness at 25° C. for 17 hr.

Results are shown in Table XII:

TABLE XII

Dependence of ALA + 2,2'-DP-Dependent Proto Accumulation and Larval Death on the Larval Species

| Experiment | Treatment of *H. zea* | Proto content (nmol/100 mg protein) | Larval death in *H. zea* after 3 days in the greenhouse (%) |
|---|---|---|---|
| A | Control | 0 | 0 |
| | Treated | 2.5 | 7 |
| | change | 2.5 | 7 |
| B | Control | 0 | 0 |
| | Treated | 1.4 | 33 |
| | change | 1.4 | 33 |

The 40 mM ALA+30 mM 2,2'-DP treatments that resulted in massive amounts of Proto accumulation and in significant larval death in *T. ni* (Tables VI-IX) resulted in a low level of Proto accumulation in *H. zea*. Larval death was also much lower than in *T. ni* (Table XII). It is not presently known whether the lower rate of Proto accumulation and concomitant lower rate of larval death in ALA+2,2'-DP-treated *H. zea* as compared to *T. ni* is due to (a) differences in the translocation of the applied chemicals to the inner tissues of the insect or (b) to some more basic biochemical differences in the regulation of the porphyrin-heme pathway between the two species. In ALA+2,2'-DP-treated *T. ni* most of the Proto accumulated in the hemolymph. This in turn indicated an adequate translocation of ALA and 2,2'-DP to the target sites. Whether these chemicals translocate as well to the inner tissues of *H. zea* is not known.

These results show that some larval species are more susceptible than others to the ALA+2,2'-DP treatment. Since it is very desirable to kill harmful insects while sparing beneficial ones, the differential susceptibility of different insect species toward porphyric insecticides may be exploited in designing species-specific porphyric insecticides.

EXAMPLE XI

Effectiveness of the ALA+2,2'-DP Treatment in the Absence of a Post-spray Dark-incubation Period Second instar *T. ni* larvae were sprayed with ALA+2,2'-DP and were subjected to a 17 h dark-incubation period before exposure to light in the greenhouse (dark-spray). Similar larvae were sprayed with ALA+2,2'-DP in the greenhouse, at the beginning of the light phase of the 14-hr light-10-hr dark photoperiod (light spray). The results of four experiments are reported in Table XIII:

TABLE XIII

Comparison of the Effectiveness of ALA + 2,2'-DP Light Sprays to Dark Sprays in *T. ni*

| Experiment | Treatment | Larval death after 3 days in the greenhouse (%) |
|---|---|---|
| A | DSP control | 21 |
|  | DSP 20 mM ALA + 15 mM 2,2'-DP | 90 |
|  | DSP Δ change | 69 |
| B | LSP control | 25 |
|  | LSP 20 mM ALA + 15 mM 2,2'-DP | 94 |
|  | LSP Δ change | 69 |
| C | DSP control | 14 |
|  | DSP 40 mM ALA + 30 mM 2,2'-DP | 93 |
|  | DSP Δ change | 79 |
| D | LSP control | 5 |
|  | LSP 40 mM ALA + 30 mM 2,2'-DP | 83 |
|  | LSP Δ change | 78 | wherein "DSP"=dark spray and "LSP"=light spray. The light sprays were as effective in causing larval death as the dark sprays. These results were in turn very similar to those of dark and light photodynamic herbicide treatments shown in U.S. Ser. No. 895,529.

EXAMPLE XII 1,10-Phenanthroline as an Inducer/Enhancer

To determine whether chemicals which exhibited inducing or enhancing tetrapyrrole properties in plants would exhibit similar properties in insects, the effect on tetrapyrrole accumulation in *T. ni* of several known enhancers and inducers of tetrapyrrole accumulation in plants was examined. Third instar *T. ni* larvae were sprayed with a solution of 40 mM ALA+30 mM 1,10-PA as described in Example III for ALA+2,2'-DP. The control and treated larvae were processed and analyzed as described in Example II. The results of these experiments are shown in Table XIV:

TABLE XIV

Synergistic Effects of ALA + 1,10-PA in Causing Proto and Zn-Proto Accumulation and Larval Death in *T. ni*

| Experiment | # | Treatment | Proto content (mMoles/100 mg protein) | Zn-Proto content (mMoles/100 mg protein) | Larval death after 3 days in the greenhouse (%) |
|---|---|---|---|---|---|
| A | 1 | Control | 0.19 | 0 | 0 |
|  | 2 | 40 mM ALA | 3.18 | 0 | 16.8 |
|  | 3 | 30 mM 1,10 PA | 35.26 | 4.45 | 69.6 |
|  | 4 | 40 mM ALA + 30 mM 1,10-PA | 151.92 | 3.75 | 93 |
| B | 1 | Control | 0 | 0 | 6.1 |
|  | 2 | 40 mM ALA | 2.08 | 0 | 5.3 |
|  | 3 | 30 mM 1,10-PA | 18.55 | 1.08 | 74.7 |
|  | 4 | 40 mM ALA + 30 mM 1,10-PA | 227.77 | 6.15 | 93.3 |
| Correlation Coefficient |  |  | 0.78[a] | 0.862[b] |  |
| Level of significance |  |  | 5% | 1% |  |

[a] Correlation between larval death and Proto accumulation
[b] Correlation between larval death and Zn-Proto accumulation As was observed with 2,2'-DP (Table VIII), 1,10-PA exhibited very strong tetrapyrrole inducing-enhancing properties, as shown by the very strong synergism in Proto accumulation which was observed when ALA and 1,10-PA were used together.

In addition to the massive accumulation of Proto, treatment with 1,10-PA in the presence or absence of ALA, resulted in the formation of smaller amounts of Zn-Proto. The correlation between Zn-Proto accumulation and larval death was highly significant. This in turn suggested that the formation of Zn-Proto was somehow strongly related to larval death.

Other experiments were designed to determine whether Zn-Proto was indeed formed enzymatically or not. For example, the addition of 1,10-PA to Proto dissolved in 80% acetone did not result in Zn-Proto formation after 17 hours of incubation. In other experiments live and dead *T. ni* larvae were treated with 40 mM ALA+30 mM 1,10-PA exactly as described in Table XIV. The dead larvae were killed by boiling in water at 100° C. for 5 minutes prior to spraying. Results are shown in Table XV:

TABLE XV

Effect of ALA + 1,10-PA Treatment on Zn-Proto and Proto Accumulation in Live Versus Dead *T. ni* Larvae

| Experiment | # | Treatment | Proto content (mMoles/100 mg protein) | Zn-Proto content (mMoles/100 mg protein) | Larval death after 3 days in the greenhouse (%) |
|---|---|---|---|---|---|
| A | 1 | Control | 0 | 0 | 0 |
|  | 2 | Dead larvae treated with 40 mM ALA + 30 mM 1,10-PA | 0 | 0 | — |
|  | 3 | Live larvae treated with 40 mM ALA + 30 mM 1,10-PA | 242.7 | 3.25 | 93.4 |
| B | 1 | Control | 0.11 | 0 | 0 |
|  | 2 | Dead larvae treated with 40 mM ALA + 30 mM 1,10-PA | 0 | 0 | — |
|  | 3 | Live larvae treated with 40 mM ALA + 30 mM 1,10-PA | 251.23 | 4.43 | 100 |

As shown, only live insects with active metabolisms were able to accumulate Proto and In-Proto. Altogether these results strongly indicated that the formation of Proto and In-Proto by the treated insects was a consequence of enzymatic activity.

EXAMPLE XIII

Administration of the ALA+1,10-PA Treatment in the Diet

Under certain field conditions it is sometimes preferable to administer an insecticide as a bait rather than as a spray. The following experiments were therefore designed to demonstrate the effectiveness of porphyric insecticides when administered as bait.

In one experiment, food cubes of Waldbauer's medium were sprayed at a total rate of 1.5 ml per 10 ml of solid diet. One third of the volume was sprayed at a time. The diet cubes were allowed to dry, then the process was repeated two more times. Untreated larvae were then placed with the treated diet in darkness for 17 hours. Alternatively, the larvae, together with their diet, were sprayed exactly as in Example III. Results are shown in Table XVI:

TABLE XVI

Effect of ALA+1,10-PA Addition to the Diet upon *T. ni* Larval Death

| # | Treatment | Larval death within the first 8 min in the light (%) | Larval death after 3 days in the greenhouse (%) |
|---|---|---|---|
| 1 | Control | 0 | 2.2 |
| 2 | Diet only sprayed with 40 mM ALA + 30 mM 1,10-PA | 62.5 | 95.9 |
| 3 | Diet and insect sprayed with 40 mM ALA + 30 mM 1,10-PA | 91.2 | 96.7 |

As shown, application of the chemicals solely via the food was as effective in causing larval death as in spraying both the insect and its diet. Furthermore, it was observed that most of the larval death in insects that ingested the treated diet occurred during the first 8 minutes of exposure to light, with substantial death occurring during the first 2 minutes in the light.

In another experiment, the ALA and 1,10-PA were incorporated in the diet at a rate of 16 and 12 mM respectively. The diet was mixed with the ALA and 1,10-PA in a blender at 37° C. for 5 minutes. The larvae were placed on the baited diet for 17 hours in darkness before exposure to light. Results are shown in Table VII:

TABLE XVII

Effect of ALA + 1,10-PA Addition to the Diet upon *T. ni* Larval Death

| # | Treatment | Larval death within the first 8 min in the light (%) | Larval death after 3 days in the greenhouse (%) |
|---|---|---|---|
| 1 | Control | 0 | 4 |
| 2 | Diet containing 16 mM ALA + 12 mM 1,10-PA | 91.9 | 100 |

In another experiment, the diet was heated in a convection oven and the ALA and 1,10-PA were added to the heated diet at 57° C. The mixture was then blended for 45 seconds in a Sorval Omnimixer (Omni Co. Interrnational, CT 06706). Results are shown in Table XVIII:

TABLE XVIII

Effect of ALA + 1,10-PA Addition to the Diet upon *T. ni* Larval Death

| # | Treatment | Larval death within the first 8 min in the light (%) | Larval death after 3 days in the greenhouse (%) |
|---|---|---|---|
| 1 | Control | 0 | 14.5 |
| 2 | Diet containing 16 mM ALA | 0 | 5.2 |
| 3 | Diet containing 12 mM 1,10-PA | 0 | 40.4 |
| 4 | Diet containing 16 mM ALA + 12 mM 1,10-PA | 94.4 | 94.4 |

As shown in Table VII(2) and VIII(4), incorporation of the chemicals in the diet resulted in an excellent measure of larval death. The same synergism between ALA and 1,10-PA was observed as when the two chemicals were applied as a spray (Table XV vs. Table VIII).

Altogether these results indicate that porphyric insecticides can be effective either as sprays or baits.

EXAMPLE XIV

Administration of Alternative Inducers and/or Enhancers

Waldbauer's medium was heated in a convection oven to 57°–65° C. and combined with 4 mM ALA and 3 mM of one of various test compounds. The mixture was then blended for 2 minutes in a Sorval Omnimixer.

*T. ni* larvae were placed with the treated diet in darkness for 17 hours as above. Larval death was determined at the end of the dark period (before exposure to light) and after three days in the greenhouse.

A control consisting of blank (untreated) diet was run for each compound tested.

Results are shown in Table XIX:

TABLE XIX

Effect of ALA + Various Alternative Inducers and/or Enhancers in the Diet on *T. ni* Larval Death

| | Control | Larval death at end of dark period (%) | Larval death after 3 days in the greenhouse (%) |
|---|---|---|---|
| 1,10-phenanthroline | 0 | 0 | 100 |
| 4,7-dimethyl-1,10-phenanthroline | 0 | 0 | 100 |
| 4-methyl-1,10,phenanthroline | 0 | 0 | 99 |
| 5-nitro-1,10-phenanthroline | 0 | 0 | 99 |
| 5-methyl-1,10-phenanthroline | 0 | 0 | 97 |
| 5,6-dimethyl-1,10-phenanthroline | 0 | 0 | 97 |
| 4,7-diphenyl-1,10-phenanthroline | 0 | 0 | 97 |
| 5-chloro-1,10-phenanthroline | 0 | 0 | 96 |
| 3,4,7,8-tetramethyl-1,10-phenanthroline | 0 | 0 | 85 |
| 2,2'-dithiobis(pyridine N-oxide) | 0 | 0 | 73 |
| 4,4'-dimethyl-2,2'-dipyridyl | 0 | 0 | 71 |
| phenyl 2-pyridyl ketoxime | 0 | 0 | 71 |
| 2,2':6',2''-terpyridine | 0 | 0 | 70 |
| 4,7-dihydroxy-1,10-phenanthroline | 0 | 0 | 49 |
| 2,9-dimethyl-4,7-diphenyl-1,10-phenanthroline | 0 | 0 | 39 |
| niflumic acid | 0 | 0 | 35 |
| N-benzyl-N-nicotinoyl-nictotinamide | 0 | 0 | 34 |
| dimidium bromide monohydrate | 0 | 0 | 24 |
| nicotinic acid | 0 | 0 | 22 |
| ethidium bromide | 0 | 0 | 16 |
| phenanthrene | 0 | 0 | 13 |
| ethyl nicotinate | 0 | 0 | 9 |
| 3-hydroxypicolinic acid | 0 | 0 | 9 |
| bathocuproinedisulfonic acid | 0 | 0 | 8 |
| 2-hydroxynicotinic acid | 0 | 0 | 8 |
| 4-hydroxy-7-methyl-1,8-naphthyridine-3-carboxylic acid | 0 | 0 | 8 |
| 1-isoquinoline carboxylic acid | 0 | 0 | 6 |
| picolinic acid | 0 | 0 | 5 |
| 2-hydroxy-6-methylpyridine-3-carboxylic acid | 0 | 0 | 4 |
| N-methylnicotinamide | 0 | 0 | 4 |
| benzyl viologen dichloride monohydrate | 0 | 0 | 0 |
| 1,1-diheptyl-4,4'-bipyridinium dibromide | 0 | 0 | 0 |
| 4-hydroxy-7-trifluoromethyl-3-quinoline carboxylic acid | 0 | 3 | 16 |
| diethyl-3,4-pyridine dicarboxy- | 0 | 3 | 11 |

TABLE XIX-continued

Effect of ALA + Various Alternative Inducers and/or Enhancers in the Diet on *T. ni* Larval Death

| | Control | Larval death at end of dark period (%) | Larval death after 3 days in the greenhouse (%) |
|---|---|---|---|
| late methyl nicotinate | 0 | 1 | 9 |

Repeated trials with 4 mM ALA alone gave larval death after three days in the greenhouse which consistently ran between 0 and 5%. Thus, the above results clearly show that 1,10-phenanthroline; 4,7-dimethyl-1,10-phenanthroline; 4-methyl-1,10-phenanthroline; 5-nitro-1,10-phenanthroline; 5,6-dimethyl-1,10-phenanthroline; 5-chloro-1,10-phenanthroline; 3,4,7,8-tetramethyl-1,10-phenanthroline; 2,2'-dithiobis(pyridine N-oxide); 4,4'-dimethyl-2,2'-dipyridyl; phenyl 2-pyridyl ketoxime; and 2,2':6',2''-terpyridine function as inducers and/or enhancers of ALA and are effective light-active insecticides.

EXAMPLE XV

Effect of ALA and 1,10-Phenanthroline on Larvae of *Mamestra brassicae*

The effect of ingested insecticide comprising ALA and 1,10-phenanthroline was tested on the larvae of *Mamestra brassicae*, an important pest in cruciferous vegetables.

The diet was prepared in a stainless steel bowl using a Kenwood kitchen blender as follows:

1. 1530 ml demineralized water, 504 g ground corn (maximum particle size 1 mm), 135 g brewery yeast, and 135 g wheat germ were combined at room temperature.
2. 5.4 g parahydroxymethylbenzoate was diluted in 12 ml ethanol at 90° C. and the entire 12 mls were added to the mixture of step (1) above.
3. 1530 ml of water were combined with 72 g agar and 6 g benzoic acid and the mixture was brought to a boil. The mixture was allowed to cool to 70° C. abd was then added to the mixture resulting from step (2) above.
4. The mixture resulting from step (3) above was allowed to cool to 40° C. and 18 g ascorbic acid was added as an oxidation retardant.
5. The resulting mixture was homogenized and stored for use as the standard diet.

Treated diet was prepared by dissolving an appropriate amount(s) of active ingredient(s) in ethanol and adding 1 ml of this solution to 9 ml of demineralized water. All 10 mls of the resulting ethanol:water (1:9 v/v) solution containing the appropriate amount(s) of active ingredient(s) was then added to the mixture resulting from step (3) above, before the addition of ascorbic acid.

Colonies of *M. brassicae* were mass-reared on standard (untreated) diet. As the larvae approached the third instar, batches of 20 larvae each were switched from standard diet to various test diets containing active ingredient(s). The dishes were wrapped in aluminum foil and the larvae were allowed to feed on the test diet ad libitum during a 16-hour dark period. Thereafter, the foil was removed and the larvae were exposed to artificial light (400 watt Mercury vapor lamp at 50 cm). The controls were fed untreated diet. Results are shown in Table XX:

TABLE XX

Effect of ALA and 1,10-Phenanthroline on Larvae of *M. brassicae*

| | % Mortality | |
|---|---|---|
| | Prior to light exposure | After exposure to light for 2 minutes |
| 16 mM ALA + 12 mM 1,10-phenanthroline | 0 | 100 |
| 2 mM ALA + 1.5 mM 1,10-phenanthroline | 0 | 100 |
| Control | 0 | 0 |

The effect of exposure to light is dramatic: immediately upon exposure, the treated insects began to writhe and die. 100% of the treated insects were dead within two minutes. This experiment was repeated three times with identical results.

EXAMPLE XVI

Effect of ALA and 6-Aminonicotinamide on Adult *Blatella germanica*

The effect of ingested insecticide comprising ALA and 6-aminonicotinamide was tested on the household pest *Blatella germanica* (German cockroach).

The standard diet comprised a mixture of ground grains (corn, wheat, rice, and wheat bran), cane sugar, soy protein, eggs, fennel extract, complete feed for laboratory mice, and demineralized water.

Treated feed was prepared by dissolving an appropriate amount of the active ingredient(s) in ethanol, combining 1 part of this ethanol solution with 19 parts of water, and adding 1 ml of the resulting solution to 5 g feed. The food was allowed to dry before use.

Colonies of *B. germanica* were mass-raised on standard (untreated) diet to the adult stage. On a early afternoon in November in Marseilles, France, ten adult males were placed into each of three Petrie dishes along with 5 g of one of the test diets. The dishes were allowed to sit on the bench top, receiving ordinary room light (fluorescent plus daylight), for the rest of the day (about 3.5 hrs). The dishes were further allowed to sit under ordinary room conditions (ambient light and temperature) for four days to simulate ordinary household conditions. They were exposed to natural darkness during each night for about 13 hours and to ambient light for about 11 hours during each day. A fourth dish of controls were fed standard (untreated) diet. Mortality counts were conducted each afternoon. Results are given in Table XXI:

TABLE XXI

Effect of ALA and 6-Aminonicotinamide on Adult *B. germanica*

| Active ingredient | Concentration (mg/g feed) | % Mortality Days of Exposure | | | |
|---|---|---|---|---|---|
| | | 1 | 2 | 3 | 4 |
| Control | 0 | 0 | 0 | 0 | 0 |
| ALA | 1 | 0 | 0 | 0 | 0 |
| Aminonicotinamide | 1 | 0 | 0 | 0 | 0 |
| ALA + 6-Aminonicotinamide | 1 + 1 | 50 | 70 | 90 | 100 |

These results clearly show that 6-aminonicotinate is an effective inducer and/or enhancer of ALA, and insecticidal compositions of the present invention can be effective against insects under ordinary indoor conditions of ambient light and darkness.

The chemical induction of insect larvae to accumulate Proto and Zn-Proto which cause larval death in darkness and in daylight provides novel insecticidal compositions and methods. We propose the term "porphyric insecticides" to refer to this phenomenon. In the light the accumulated Proto and Zn-Proto disappear from the insect tissues within hours. This approach is similar to the design of photodynamic herbicides shown in U.S. Ser. No. 895,529. However, damage to the plants treated with said herbicides occurred only in daylight and was exclusively photodynamic in nature. Furthermore, the most damaging tetrapyrroles were Mg-tetrapyrroles that belonged to the Chl biosynthetic pathway.

It is believed that the Mg branch of the tetrapyrrole biosynthetic pathway that leads to Chl biosynthesis is not functional in insects. As a consequence the biosynthesis of Mg-containing intermediates of the Chl biosynthetic pathway cannot be detected in $T.$ $ni$ treated with ALA or with ALA+2,2'-DP. Therefore the chlorophyllous pigments that gave the larvae its yellowish green color are most probably derived from the chlorophyllous pigments of the diet (Tables II, III, IV). All insects however do contain cytochromes which act as electron carriers in oxidative phosphorylation. It is presently believed that the heme moiety of cytochromes is formed from Proto which is synthesized in turn form ALA via the porphyrin biosynthetic pathway [Flowchart A above]. The ALA-dependent accumulation of Proto and Zn-Proto by $T.$ $ni$ is fully compatible with this hypothesis.

Contrary to what was observed in plants, the dark-accumulation of Proto in $T.$ $ni$ is accompanied by larval death in darkness (Table VII). In the light, a massive buildup of Proto does not appear to be mandatory, however, for the occurrence of photodynamic damage (Tables VII, XIII). This conclusion is based on two observations: (a) In the light, massive accumulation of Proto is not observed, probably as a consequence of the steady state photodestruction of the biosynthesized Proto (Table VII), and (b) Light-sprays (which do not involve a post-spray dark-incubation period during which Proto could accumulate) were as effective in causing larval death as dark-sprays which did include such a post-spray dark incubation period before exposure to daylight (Table XIII). Altogether these results suggest that what is needed for the occurrence of photodynamic damage in treated insects is a steady-state formation of small amounts of Proto at rates just large enough to initiate damaging free-radical chain reactions.

One of the major problems facing the insecticide industry is the alarming rate at which insects are developing resistance against insecticides. This is usually a consequence of mutations that can enhance insect detoxification mechanisms or change the lipophilic properties of the toxin, thus reducing its membrane permeability. This in turn shortens considerably the useful lifetime of newly introduced insecticides and reduces their economical value. It is believed that since the chemical modulation of the porphyrin-heme pathway according to the present invention appears to involve more than one metabolic step, it may be more difficult for insects to develop resistance against porphyric insecticides. Even if some insects succeed in developing resistance against tetrapyrrole accumulation by developing the means to rapidly destroy the accumulated tetrapyrroles, this is not likely to protect the mutated insects against photodynamic damage in the light. As is suggested by Tables VII and XIII, in the light Proto is most probably destroyed almost as rapidly as it is formed; yet such minimal accumulation is enough to cause extensive photodynamic damage to the larvae. Further, a mutation that blocks Proto and cytochrome biosynthesis altogether would most likely be lethal.

Further examples of compositions and applications within the spirit and scope of this invention will be apparent to those skilled in this art upon consideration of the foregoing and consequently only such limitations as appear in the appended claims should be placed thereon.

We claim:

1. A method for inducing the accumulation of tetrapyrroles in living insects, said method comprising contacting an insect with a composition comprising δ-aminolevulinic acid and at least one compound selected from the group consisting of inducers of δ-aminolevulinic acid, and enhancers of conversion of δ-aminolevulinic acid to tetrapyrroles.

2. The method of claim 1 wherein in the said composition the at least one compound selected from the group consisting of inducers of δ-aminolevulinic acid and enhancers of δ-aminolevulinic acid conversion to tetrapyrroles is present at a concentration of from about 0.1 to about 50 mM and the δ-aminolevulinic acid is present at a concentration of from about 2 to about 50 mM.

3. The method of claim 2 wherein said composition comprises δ-aminolevulinic acid and at least one inducer of δ-aminolevulinic acid.

4. The method of claim 2 wherein said composition comprises δ-aminolevulinic acid and at least one enhancer of δ-aminolevulinic acid conversion to tetrapyrroles.

5. The method of claim 2 wherein said composition comprises δ-aminolevulinic acid and at least one inducer of δ-aminolevulinic acid and at least one enhancer of δ-aminolevulinic acid conversion to tetrapyrroles.

6. The method of claim 1 wherein said composition further comprises at least one of the following: inert carrier(s), solvent(s), buffer(s), wetting agent(s), dispersing agent(s), defoaming agent(s), emetic(s), stench(es), penetrant(s), surfactant(s), emulsifier(s), and adjusant(s).

7. A method of killing insects, said method comprising contacting an insect with a composition comprising an insecticidally effective amount of δ-aminolevulinic acid and at least one compound selected from the group consisting of inducers of δ-aminolevulinic acid and enhancers of δ-aminolevulinic acid conversion to tetrapyrroles.

8. The method of claim 7 wherein in the said composition the at least one compound selected from the group consisting of inducers of δ-aminolevulinic acid and enhancers of δ-aminolevulinic acid conversion to tetrapyrroles is present at a concentration of from about 0.1 to about 50 mM and the δ-aminolevulinic acid is present at a concentration of from about 2 to about 50 mM.

9. The method of claim 8 wherein said composition comprises δ-aminolevulinic acid and at least one inducer of δ-aminolevulinic acid.

10. The method of claim 8 wherein said composition comprises δ-aminolevulinic acid and at least one enhancer of δ-aminolevulinic acid conversion to tetrapyrroles.

11. The method of claim 8 wherein said composition comprises δ-aminolevulinic acid and at least one inducer of δ-aminolevulinic acid and at least one enhancer of δ-aminolevulinic acid conversion to tetrapyrroles.

12. The method of claim 7 wherein said composition further comprises at least one of the following: inert carrier(s), solvent(s), buffer(s), wetting agent(s), dispersing agent(s), defoaming agent(s), emetic(s), stench(es), penetrant(s), surfactant(s), emulsifier(s), and adjuvant(s).

13. The method of claim 7 further comprising exposing said contacted insect to a substantial absence of light at wavelengths of 380 to 700 nm and then exposing said insect to light.

14. The method of claim 13 wherein said light comprises natural daylight.

15. The method of claim 13 wherein said exposure to light is for a period of about 1 to 14 days.

16. The method of claim 13 wherein said insect is exposed to light for a period of time sufficient to oxidize most unsaturated membrane lipoproteins of said insect.

17. The method of claim 13 wherein said insect is exposed to said substantial absence of light for a period of about 1 to 8 hours before being exposed to light.

18. The method of claim 13 wherein said insect is exposed to light for a period of about 2 minutes to 3 days.

19. The method of claim 7 wherein said contacted insect is exposed to a substantial absence of light at wavelengths of 380 to 700 nm.

* * * * *